(12) United States Patent
Chen (10) Patent No.: US 9,254,129 B2
(45) Date of Patent: Feb. 9, 2016

(54) SURGERY AUTOMATIC SUTURING AND KNOT TYING APPARATUS

(71) Applicant: Kuan-Ju Chen, Kaohsiung (TW)

(72) Inventor: Kuan-Ju Chen, Kaohsiung (TW)

( * ) Notice: Subject to any disclaimer, the term of this patent is extended or adjusted under 35 U.S.C. 154(b) by 363 days.

(21) Appl. No.: 14/025,120

(22) Filed: Sep. 12, 2013

(65) Prior Publication Data

US 2015/0073443 A1     Mar. 12, 2015

(51) Int. Cl.
*A61B 17/10*     (2006.01)
*A61B 17/04*     (2006.01)

(52) U.S. Cl.
CPC .......... *A61B 17/0482* (2013.01); *A61B 17/0491* (2013.01); *A61B 2017/0472* (2013.01)

(58) Field of Classification Search
CPC ........... A61B 17/0491; A61B 17/0482; A61B 17/0483
USPC ........................ 606/139, 144–148; 289/13, 17
See application file for complete search history.

(56) References Cited

U.S. PATENT DOCUMENTS

| | | | | |
|---|---|---|---|---|
| 5,389,103 A * | 2/1995 | Melzer | ............... | A61B 17/0469 112/169 |
| 5,480,406 A * | 1/1996 | Nolan | ............... | A61B 17/0469 289/1.2 |
| 5,735,862 A * | 4/1998 | Jennings | ........... | A61B 17/0491 112/169 |
| 5,908,428 A * | 6/1999 | Scirica | ............... | A61B 17/0469 206/339 |
| 5,954,731 A * | 9/1999 | Yoon | ................... | A61B 17/062 606/139 |
| 5,984,932 A * | 11/1999 | Yoon | ................... | A61B 17/0469 606/147 |
| 5,993,466 A * | 11/1999 | Yoon | ................... | A61B 17/062 606/144 |
| 6,004,332 A * | 12/1999 | Yoon | ................... | A61B 17/0469 606/139 |
| 6,017,358 A * | 1/2000 | Yoon | ................... | A61B 17/29 600/564 |
| 6,080,180 A * | 6/2000 | Yoon | ................... | A61B 17/29 606/205 |
| 6,086,601 A * | 7/2000 | Yoon | ................... | A61B 17/062 606/139 |
| 6,117,144 A * | 9/2000 | Nobles | ............... | A61B 17/0057 606/139 |
| 6,126,665 A * | 10/2000 | Yoon | ................... | A61B 17/0469 606/144 |
| 6,143,005 A * | 11/2000 | Yoon | ................... | A61B 17/0469 606/148 |
| 6,159,224 A * | 12/2000 | Yoon | ................... | A61B 17/0469 606/139 |
| 6,224,614 B1 * | 5/2001 | Yoon | ................... | A61B 17/062 606/147 |
| 2002/0045908 A1 * | 4/2002 | Nobles | ............... | A61B 17/0057 606/144 |
| 2012/0143223 A1 * | 6/2012 | Woodard, Jr. | ...... | A61B 17/0469 606/147 |

* cited by examiner

*Primary Examiner* — Todd E Manahan
*Assistant Examiner* — Charles Wei
(74) *Attorney, Agent, or Firm* — Muncy, Geissler, Olds & Lowe, P.C.

(57) ABSTRACT

A surgery automatic suturing and knot tying apparatus is to suture and tie knots on a surgical suture having a needle end and a tail end. The surgery automatic suturing and knot tying apparatus comprises a positioning board, a threading module located on the positioning board, and two thread drawing modules and two needle threading arms located on the positioning board. The two needle threading arms wind the surgical suture around the threading module, and collaborate with the two thread drawing modules to draw the surgical suture to make the surgical suture finally be separated from the threading module, thereby can tie knots automatically on the surgical suture to meet use requirements and alleviate the burden of doctors during surgical operation.

8 Claims, 11 Drawing Sheets

SURGERY AUTOMATIC SUTURING AND KNOT TYING APPARATUS

FIELD OF THE INVENTION

The present invention relates to a surgery ancillary apparatus and particularly to a surgery automatic suturing and knot tying apparatus.

BACKGROUND OF THE INVENTION

In surgical operation suturing is a necessary skill needed by doctors. Suturing of wounds on patient's skin is simpler, and doctors usually can stitch the wound with a suturing needle and a suture. Duration of surgery often affects patient's survival probability and patient's recuperation. Hence to shorten surgery duration is a heavy focus for doctors and medical instrument developers.

Aside from the practice of suturing and tying knots manually on the wounds adopted by the surgeons, to speed up the suturing time a surgery suturing stapler has been disclosed in the conventional technique. It mainly pushes staples through a biased spring to seal the surgical incision. But suturing via the staples still does not provide firm holding as desired, hence patients have to take great care to avoid stretching or moving the wounds after surgery to prevent the staples from loosening off.

U.S. Pat. No. 5,480,406 discloses a "Method of employing surgical suturing apparatus to tie knots". It proposes a surgery knot tying apparatus which mainly includes a suturing device and a clamping device. The suturing device has two jaws which can alternately hold a needle. At two sides of an object where suturing is to be performed, one jaw can hold the needle to pass through the object and then another jaw holds the needle, thereby threading operation of the needle can be quickly performed at two sides of the object. Knot tying operation can be performed manually collaborating with the clamping device. The method mentioned above not only can be adopted for suturing patient's skin since the suturing device and clamping device are made in a smaller size, but also can be used in suturing the internal organs of the patients. However, users need to have good three dimensional space concept and undergo a great deal of practices to skillfully use the suturing device and the clamping device to tie the knots and perform suturing quickly. It still leaves a lot to be desired in terms of meeting the expectation of people doing research and development in surgery instruments. There is still room for improvement.

SUMMARY OF THE INVENTION

The primary object of the present invention is to solve the problems of the conventional techniques that rely on manual operation for tying knots in surgery and require doctors to do a great deal of practices in tying knots via instruments to become skillful in use that result in shortfall in meeting use requirements.

To achieve the foregoing object, the present invention provides a surgery automatic suturing and knot tying apparatus to suture and tie knots on a surgical suture having a needle end and a tail end. The surgery automatic suturing and knot tying apparatus comprises a positioning board, a threading module located on the positioning board, and two thread drawing modules and two needle threading arms located on the positioning board. The positioning board has a knot tying side and an operation side at two sides thereof, and two thread drawing apertures communicating with the knot tying side and operation side.

The threading module is located on the positioning board between the two thread drawing apertures and includes a threading rack located at the knot tying side and a clamping member connected to the threading rack. The threading rack has a bend section, an opening at one end of the bend section remote from the positioning board and a lower threading space inside the bend section to communicate with the opening. The clamping member is located at one end of the bend section abutting the opening. The bend section and positioning board are interposed by an upper threading space corresponding to the lower threading space.

The two thread drawing modules are located on the positioning board corresponding to the two thread drawing apertures and at two sides of a plane formed by the lower threading space, and have respectively a lift mechanism running through one thread drawing aperture and a thread drawing member located on the lift mechanism. The thread drawing member is moved reciprocally between the knot tying side and operation side via the lift mechanism. The two needle threading arms are located at two sides of the two thread drawing modules remote from the threading rack, and are at the knot tying side of the positioning board to swivel about the positioning board serving as an axis towards the threading rack.

The clamping member clamps the tail end of the surgical suture. The two needle threading arms alternately hold a needle at the needle end to pass through the upper threading space and lower threading space of the threading module, and collaborate with the two thread drawing modules to tie knots on the surgical suture at the opening.

By means of the technique set forth above, through operation of drawing the surgical suture reciprocally in the threading module via the two needle threading arms and the two thread drawing modules, the surgical suture can be tied to form knots at the opening. The apparatus thus formed provides features as follow:

1. Tying the knots in a fully automatic fashion at the surgery suturing location and can be operated by surgeons without additional practice, hence relieves surgeons' heavy burden from prolonged practices to get the skills needed.

2. Aids doctors during suturing the wounds in the surgical operation to alleviate the burden of the doctors.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
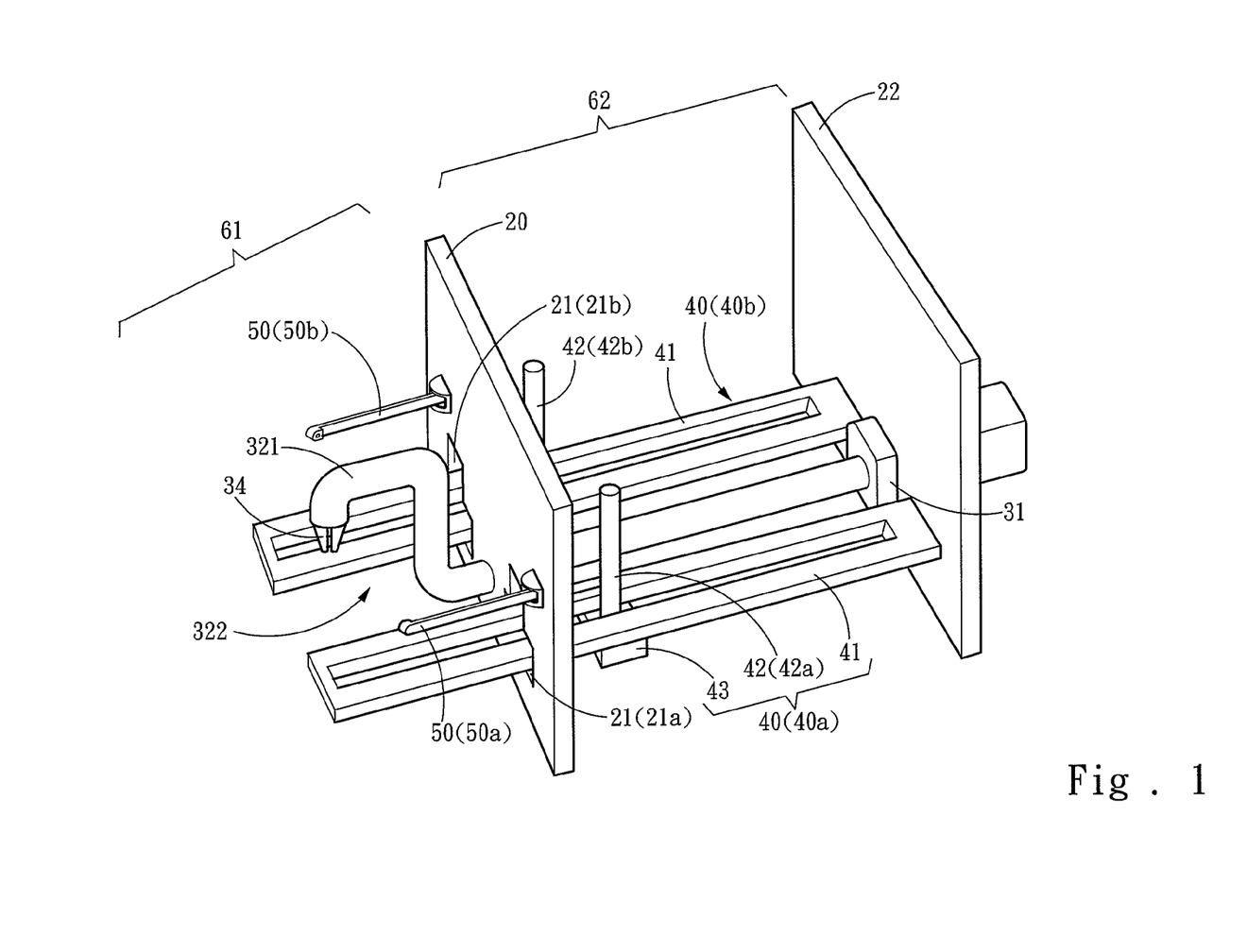
FIG. 1 is a perspective view of the invention.
Figure 2:
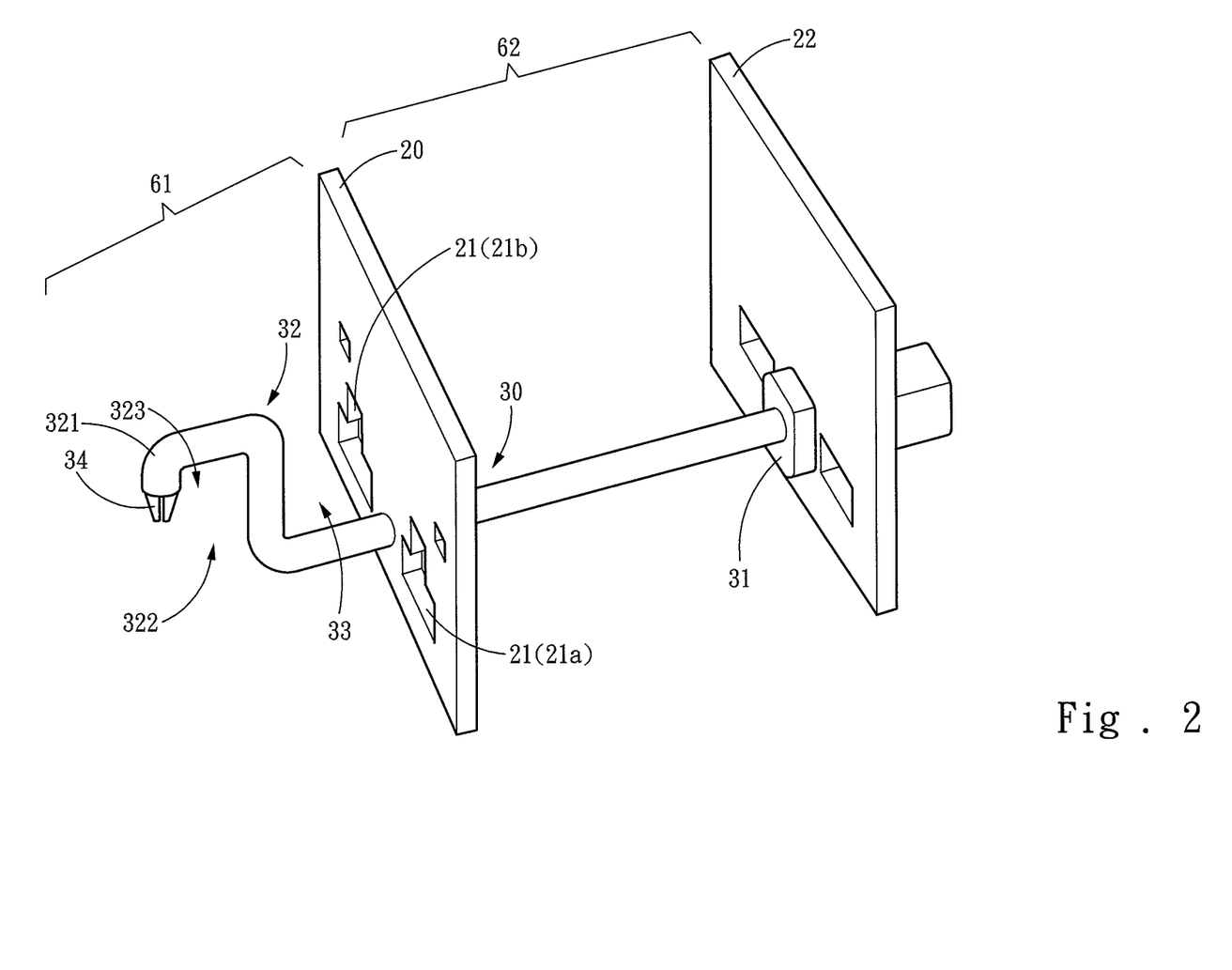
FIG. 2 is a perspective view of the threading module of the invention.

Please refer to FIGS. 1 and 2, the present invention aims to provide a surgery automatic suturing and knot tying apparatus to suture and tie knots on a surgical suture 10 having a needle end 11 and a tail end 12. The apparatus comprises a positioning board 20, a threading module 30 located on the positioning board 20, and two thread drawing modules 40 and two needle threading arms 50 located on the positioning board 20. The positioning board 20 has a knot tying side 61 and an operation side 62 at two sides thereof. The positioning board 20 also has two thread drawing apertures 21 communicating with the knot tying side 61 and operation side 62. In this embodiment the operation side 62 has an anchor board 22 spaced from the positioning board 20 at a selected distance. The threading module 30 and thread drawing modules 40 can be mounted onto the positioning board 20 and anchor board 22 to perform corresponding operations.

The threading module 30 is located on the positioning board 20 between the two thread drawing apertures 21, and includes a vertical movement unit 31 connected to the positioning board 20, a threading rack 32 connected to one end of the vertical movement unit 31 at the knot tying side 61, and a clamping member 34 connected to the threading rack 32. The threading rack 32 has a bend section 321 connected to the vertical movement unit 31, an opening 322 located at one end of the bend section 321 remote from the vertical movement unit 31 and a lower threading space 323 located on the bend section 321 communicating with the opening 322. The vertical movement unit 31 drives the threading rack 32 to move vertically towards the positioning board 20. The clamping member 34 is located at one end of the bend section 321 abutting the opening 322. It is to be noted that the vertical movement unit 31 can drive the threading rack 32 to move vertically to an upper threading position remote from the positioning board 20 as shown in FIG. 2, and a lower threading position abutting the positioning board 20 as shown in FIG. 1.

The two thread drawing modules 40 are located on the positioning board 20 corresponding to the two thread drawing apertures 21. In addition, the two thread drawing modules 40 also are located at two sides of a plane formed by the lower threading space 323. Each thread drawing module 40 has a lift mechanism 41 running through the thread drawing aperture 21 and a thread drawing member 42 located on the lift mechanism 41. The thread drawing member 42 is moveable reciprocally through the lift mechanism 41 between the knot tying side 61 and operation side 62. It also to be noted that the thread drawing module 40 further has a swivel member 43 located on the lift mechanism 41. The thread drawing member 42 is a rod fixedly mounted onto the swivel member 43 and extended in a direction remote from the lift mechanism 41. The swivel member 43 drives the thread drawing member 42 to swivel in the moving direction of the lift mechanism 41. Moreover, in this embodiment, the two thread drawing modules 40 are located at one side of the positioning board 20 abutting the opening 322. The thread drawing member 42 is a rod extended from the opening 322 towards the bend section 321. It is to be noted that the thread drawing modules 40 also can be located at two opposing sides abutting the opening 322 and remote from the opening 322 respectively; in such a condition, the two thread drawing members 42 are extended in opposing directions. Moreover, the lift mechanism 41 also can be bent to form non-linear track or can be made of flexible material to facilitate surgical operation at specific angle.

The two needle threading arms 50 are located at two sides of the two thread drawing modules 40 remote from the threading rack 32, and also at the knot tying side 61 of the positioning board 20, and can swivel about the positioning board 20 serving as an axis towards the threading rack 32. The clamping member 34 clamps the tail end 12 of the surgical suture 10. The two needle threading arms 50 alternately hold a needle 13 at the needle end 11 to pass through the threading module 30 and collaborate with the two thread drawing modules 40 to tie knots on the surgical suture 10 at the opening 322.

Please refer to FIGS. 3A through 3F for the invention in operating conditions.

Figure 3A:
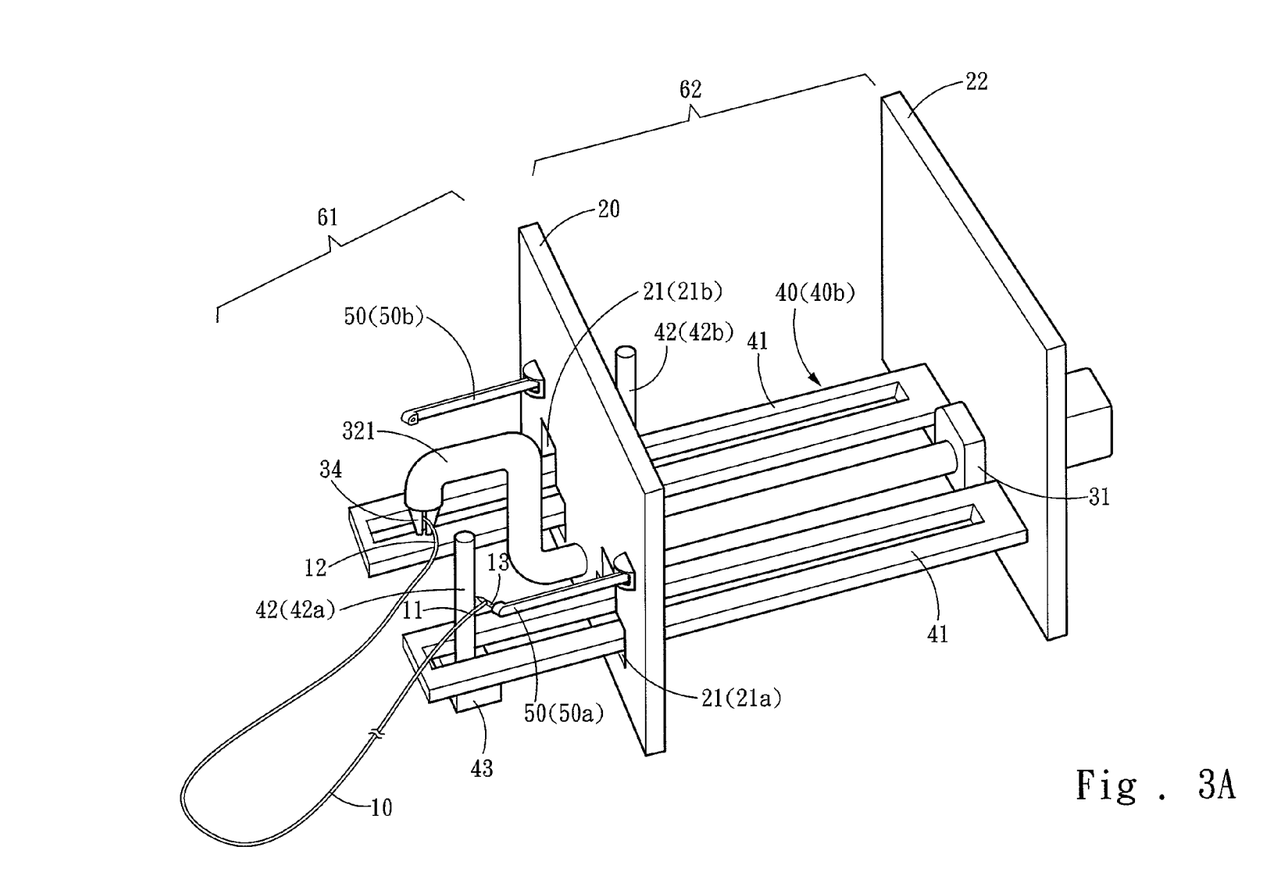
FIGS. 3A through 3F are schematic views of knot tying operation procedures according to the invention.

First, referring to FIG. 3A, the needle end 11 of the surgical suture 10 is connected to a needle 13 and the tail end 12 is connected to the clamping member 34 of the threading module 30. It is assumed that the surgical suture 10 has already passed through the wound desired to be sutured and tied a knot, the tail end 12 is at one side of the wound and the surgical suture 10 passes through the wound and the needle 13 is held by the needle threading arm 50. The two needle threading arms 50 are defined as a first needle threading arm 50a and a second needle threading arm 50b. The two thread drawing modules 40 are defined as a first thread drawing module 40a and a second thread drawing module 40b with corresponding first thread drawing member 42a and second thread drawing member 42b. The needle 13 is held by the first needle threading arm 50a.

Figure 3B:
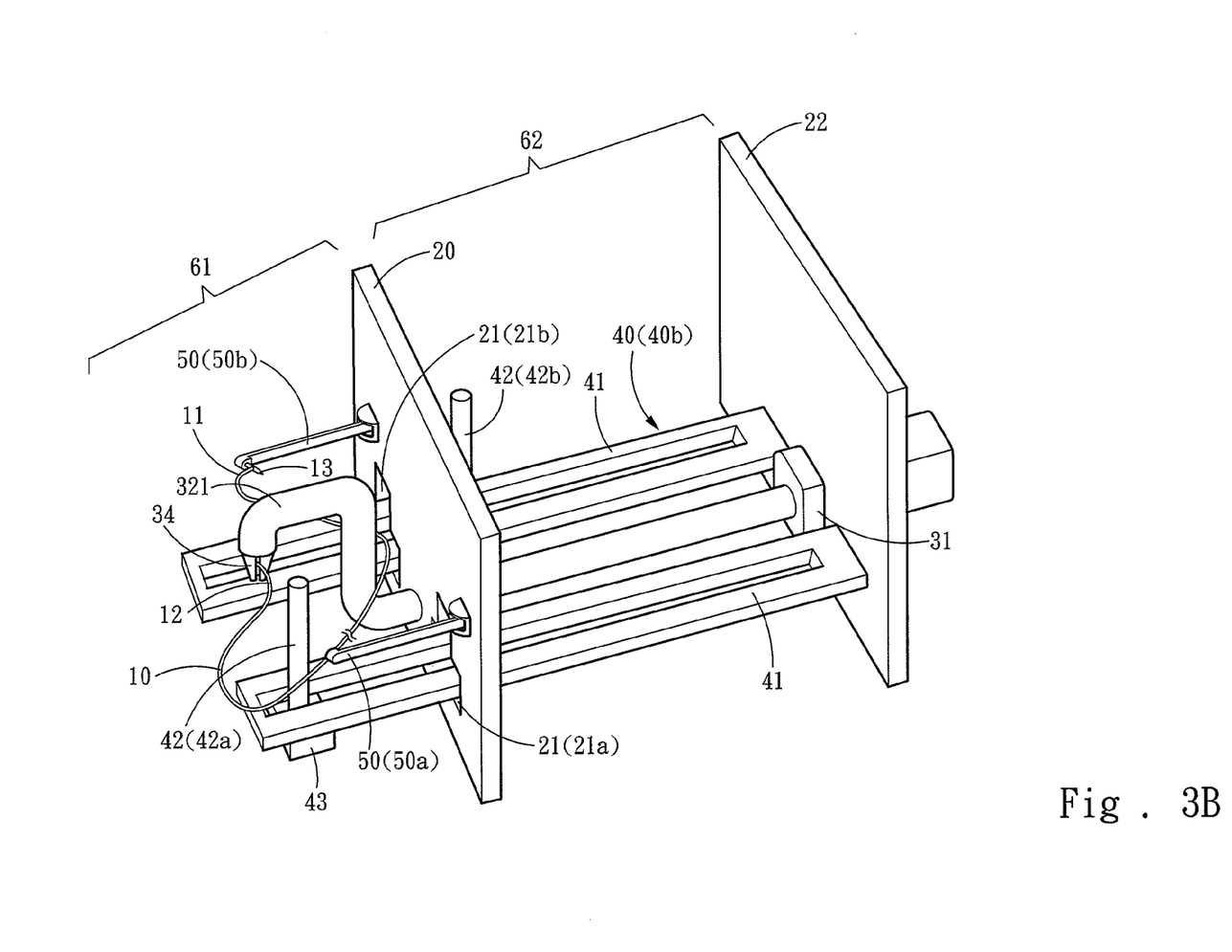
Figure 3C:
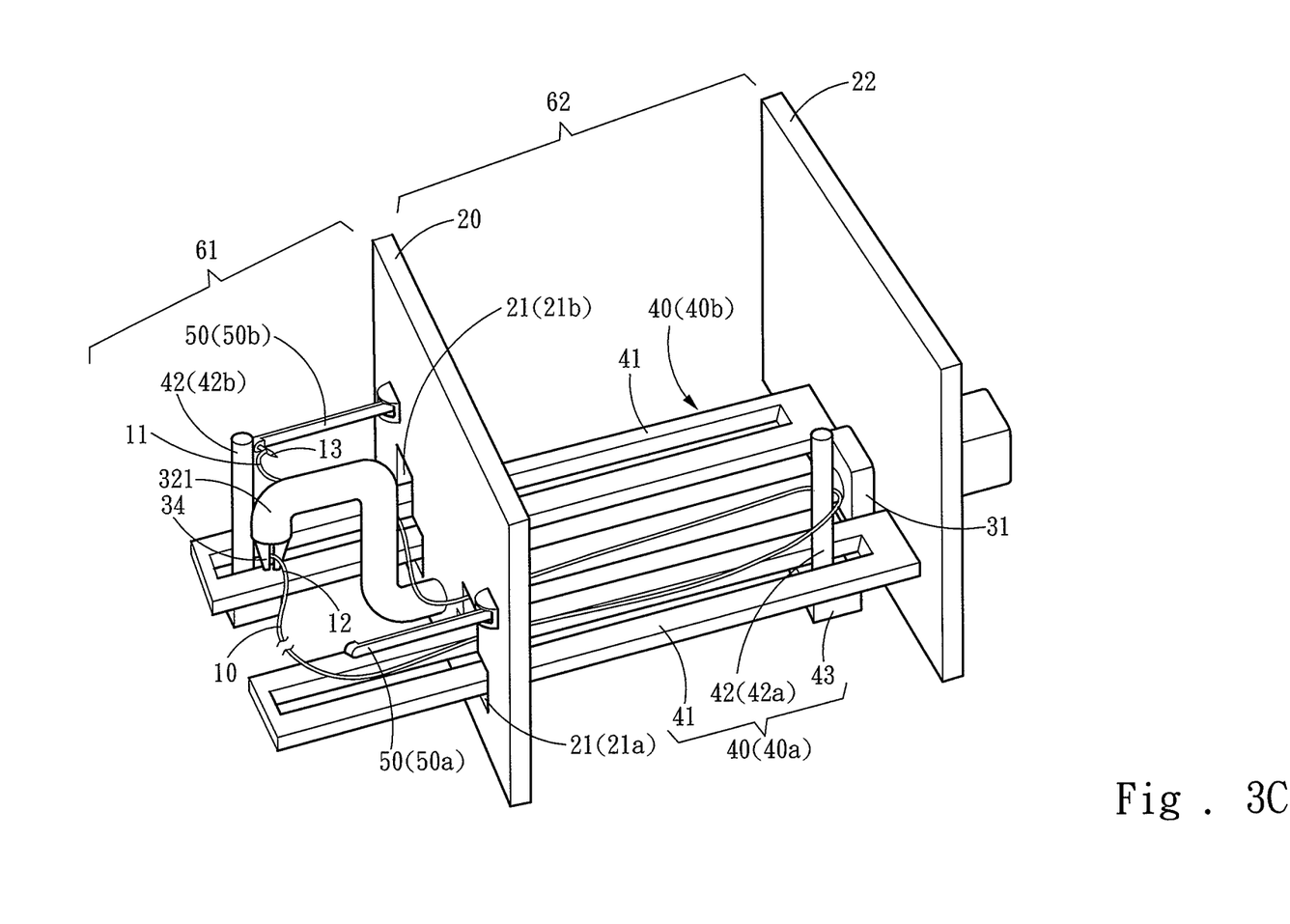

Next, the vertical movement unit 31 is moved to the upper threading space 33 formed between the bend section 321 and positioning board 20; the first needle threading arm 50a and second needle threading arm 50b are close to each other in the upper threading space 33, and the needle 13 at the first needle threading arm 50a is shifted to the second needle threading arm 50b to allow the surgical suture 10 to pass through the upper threading space 33 as shown in FIG. 3B. Meanwhile, the surgical suture 10 passes through between the first thread drawing member 42a and positioning board 20. Through the lift mechanism 41, the first thread drawing member 42a passes through the first thread drawing aperture 21a and moves towards the operation side 62 so that the surgical suture 10 is drawn to the operation side 62 with the first thread drawing member 42a as shown in FIG. 3C. It is to be noted that in this embodiment the angle of the first thread drawing member 42a can be adjusted through turning of the swivel member 43 to pass through the thread drawing aperture 21 and draw the surgical suture 10 without dropping.

Figure 3D:
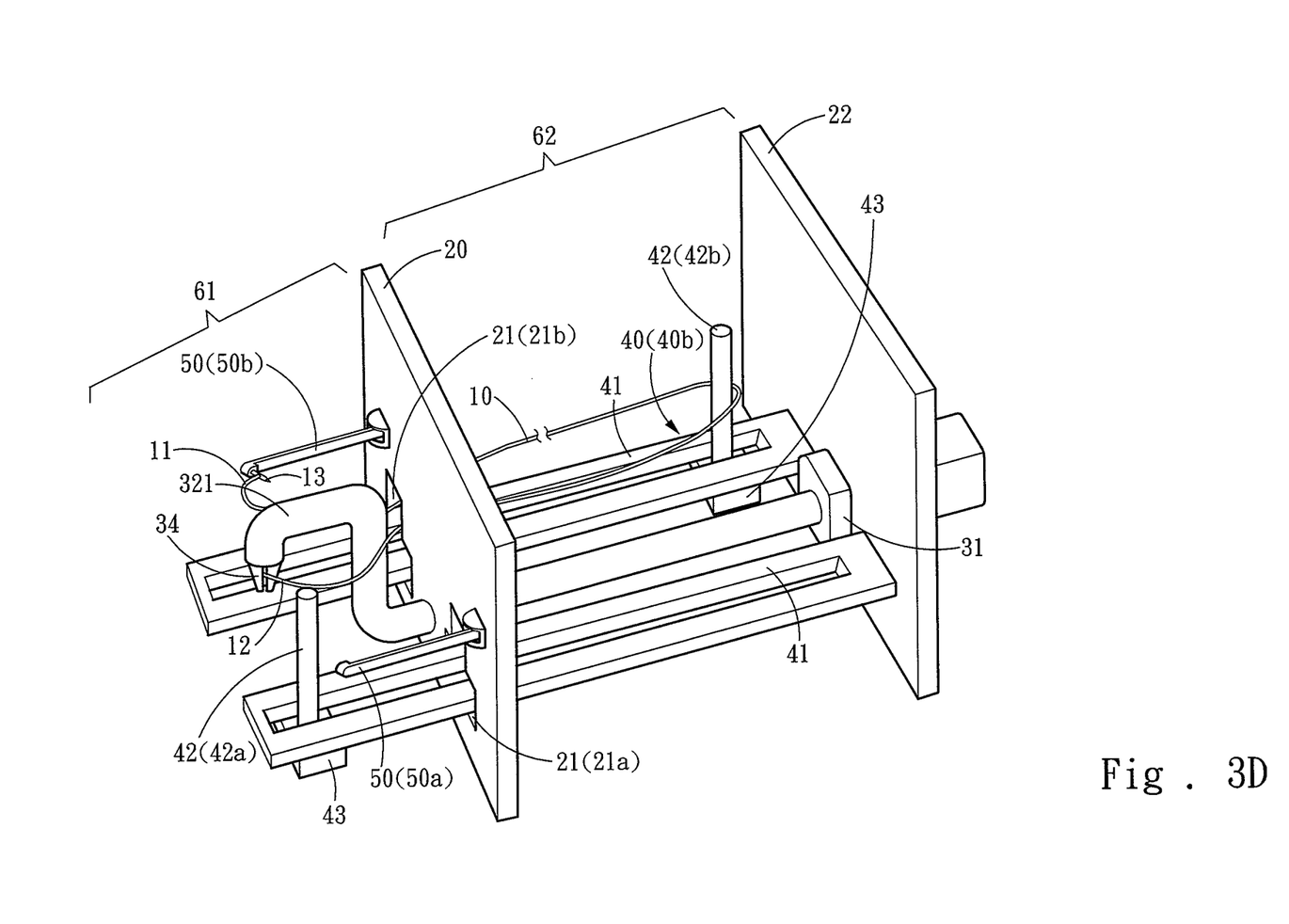
Figure 3E:
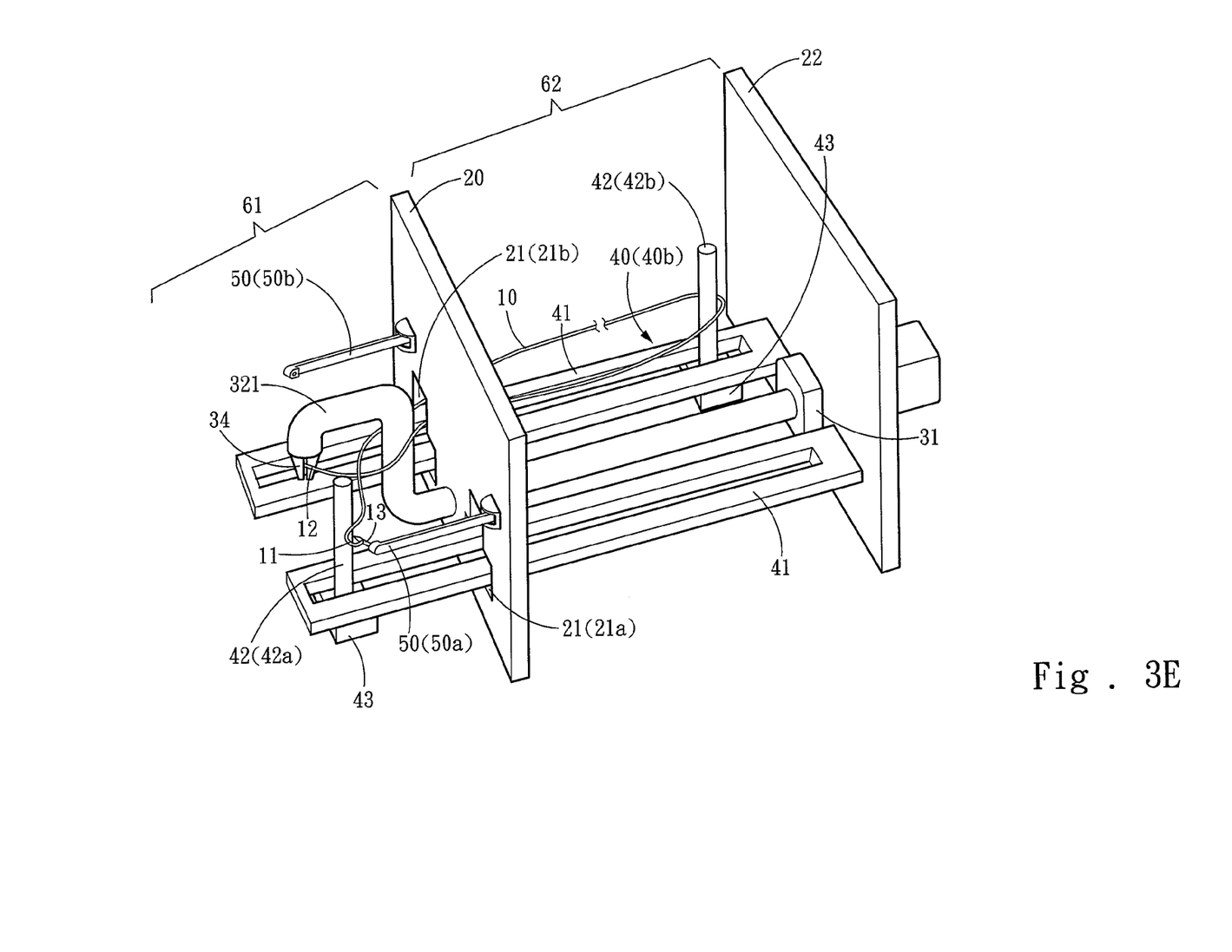
Figure 3F:
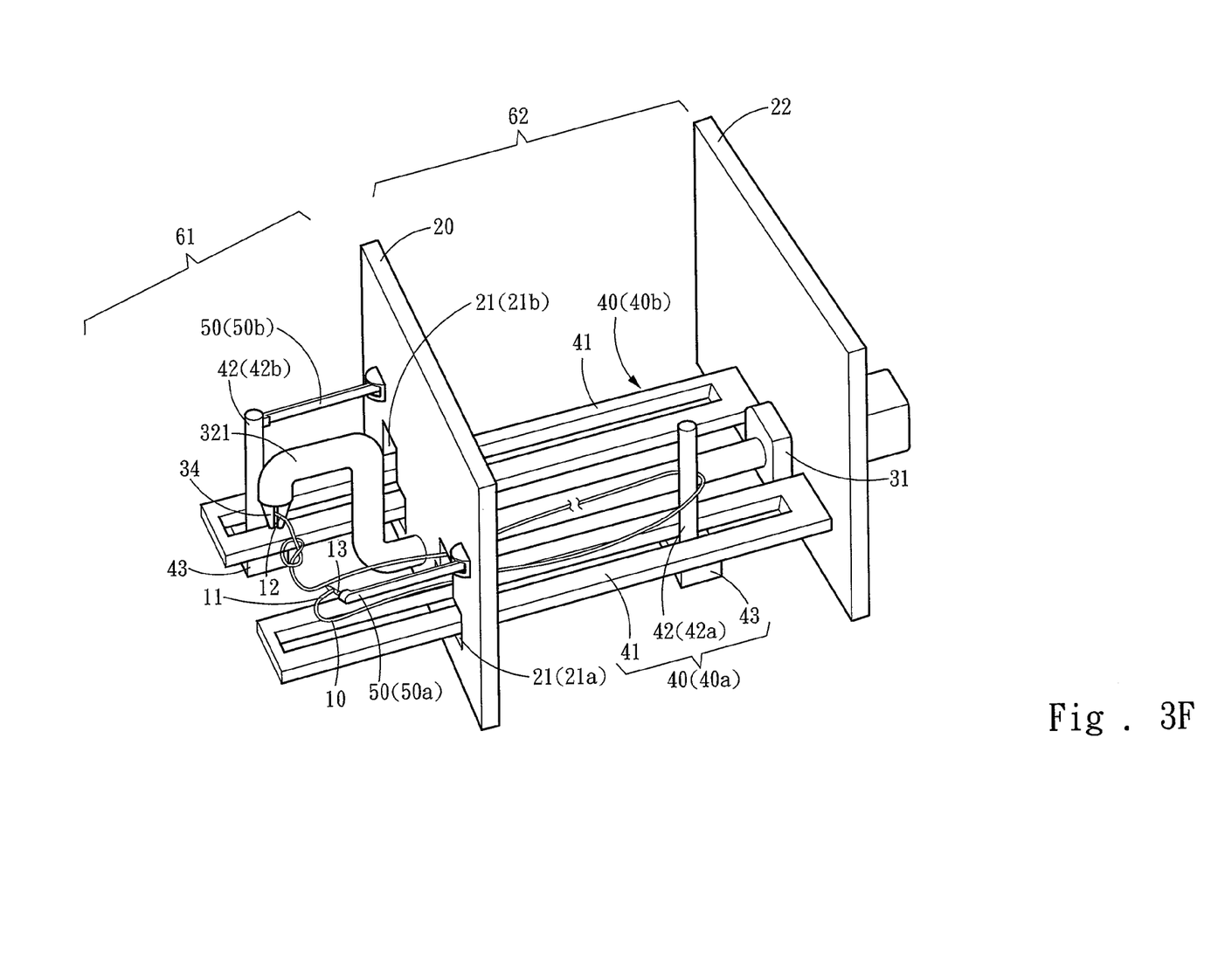
Figure 4:
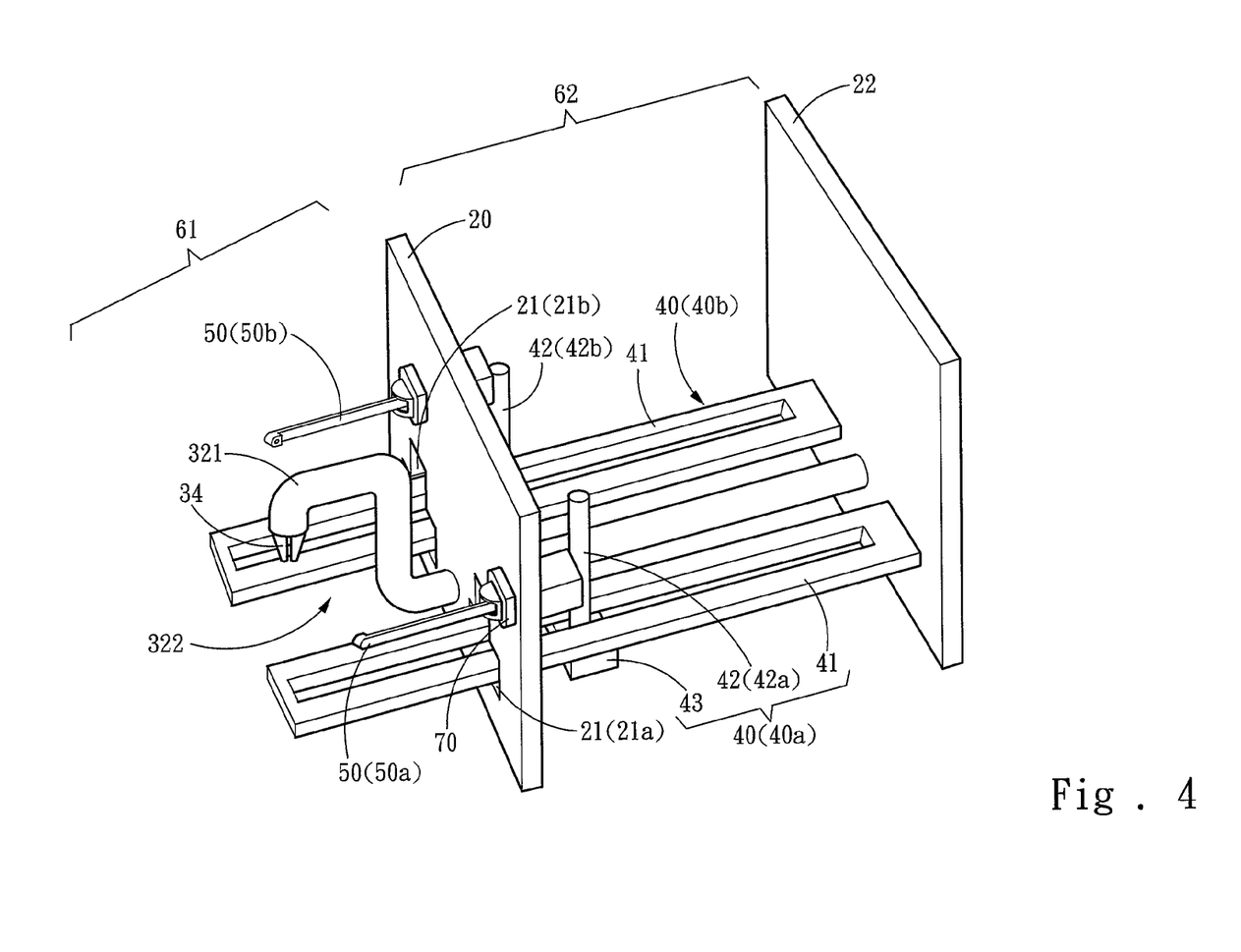
FIG. 4 is a perspective view of a second embodiment of the invention.

Then, referring to FIG. 3D, the second thread drawing member 42b draws the surgical suture 10 to pass through the second thread drawing aperture 21b from the knot tying side 61 and move towards the operation side 62; meanwhile, the first thread drawing member 42a is moved from the operation side 62 to the knot tying side 61, thereby the surgical suture 10 is moved from the first thread drawing module 40a to the second thread drawing module 40b. Also referring to FIG. 3E, the second needle threading arm 50b and first needle threading arm 50a are moved close to each other by swiveling at the lower threading position, and the needle 13 also is shifted from the second needle threading arm 50b to the first needle threading arm 50a and held by the first needle threading arm 50a. Finally, referring to FIG. 3F, the first thread drawing member catches the surgical suture 10, and moves from the knot tying side 61 towards the operation side 62; meanwhile, the second thread drawing member moves from the operation side 62 towards the knot tying side 61, and also draws the surgical suture 10 from the clamping member 34 towards the opening 322 to release, thereby knot is tied on the surgical suture 10 at the location of the opening 322 abutting the clamping member 34 to finish the automatic knot tying process of the invention. Aside from the vertical movement unit 31 controlling the threading rack 32 to have the upper threading position and lower threading position, also referring to FIG. 4 for a second embodiment of the invention in which the apparatus of the invention includes two vertical operation units 70 connected to the two needle threading arms 50 to control the two needle threading arms 50 to move vertically towards the positioning board 20 so that the needle 13 is alternately held in the upper threading space 33 and lower threading space 323. Hence, aside from vertical movement of the threading module 30, the needle threading arms 50 also can be moved vertically to achieve the threading objective.

Figure 5:
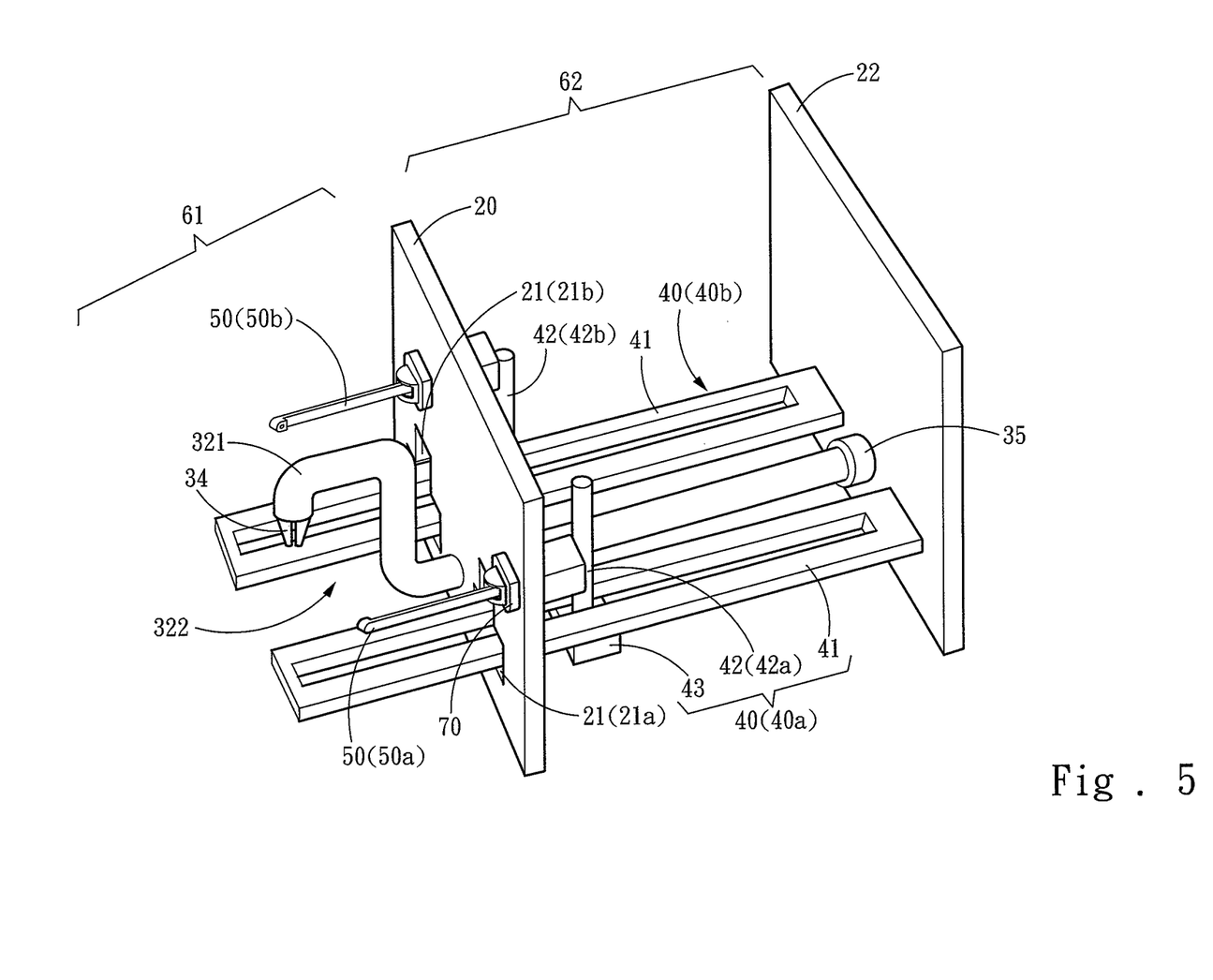
FIG. 5 is a perspective view of a third embodiment of the invention.

Please refer to FIG. 5 for a third embodiment of the invention. To avoid the surgical suture 10 from unable to separate from the bend section 321 to finish knot tying at the opening 322, the threading module 30 further includes a rotary unit 35 connected to the threading rack 32 so that the threading rack 32 can rotate about the rotary unit 35 serving as an axis to allow the surgical suture 10 to easily separate from the threading rack 32 to finish knot tying at the opening 322. The rotary unit 35 can be an active swivel means driven by an active power source, or a mechanism pivotally coupled with the threading rack 32 and swiveled passively by drawing of an external force.

Figure 6:
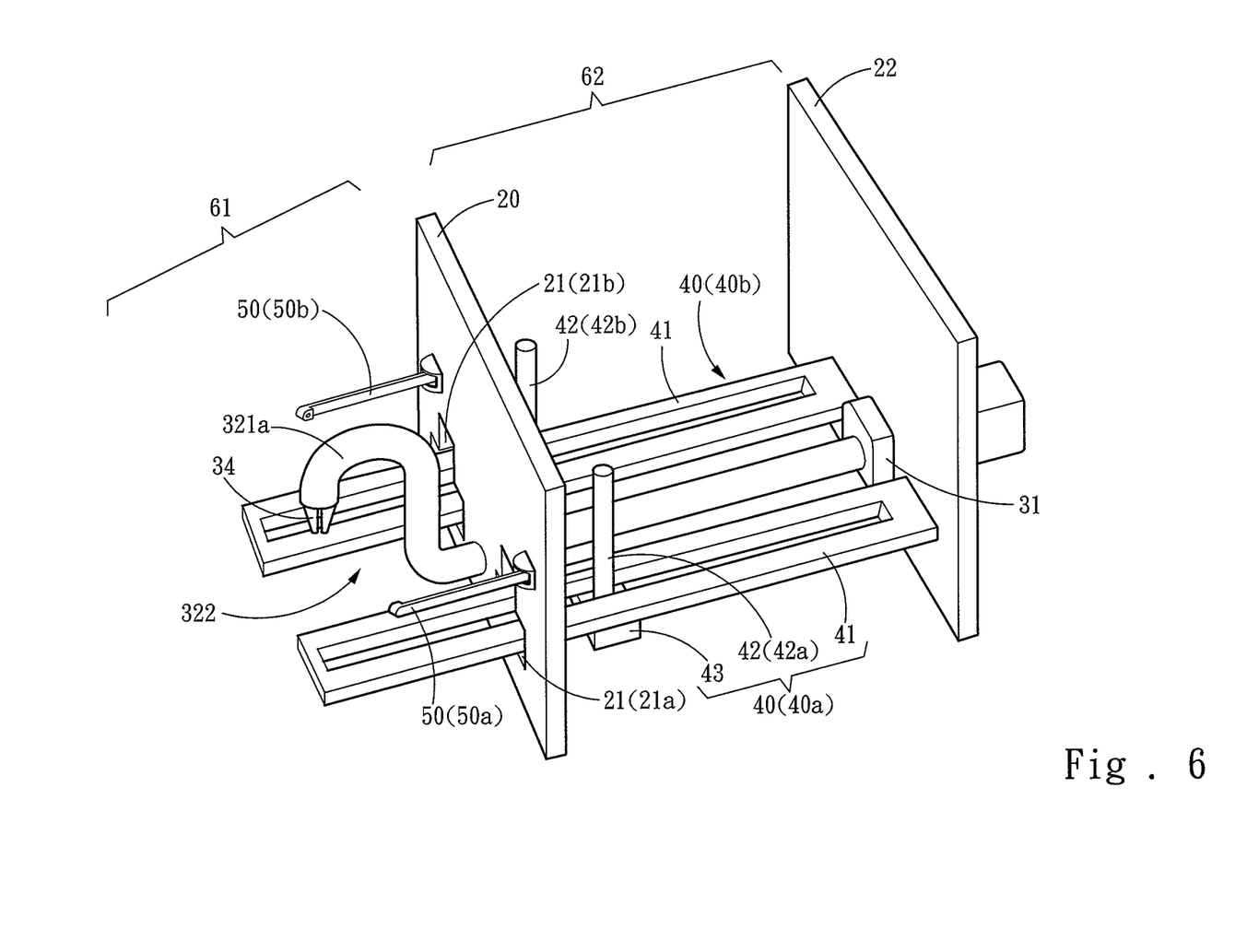
FIG. 6 is a perspective view of a fourth embodiment of the invention.

The bend section 321 of the threading rack 32, in addition to the style depicted in the previous embodiments, can also be formed in a fourth embodiment as shown in FIG. 6. In which, the bend section 321a is an arched structure to form the opening 322, i.e., formed in a C-shaped, to avoid the surgical suture 10 from being caught by the threading rack 32 during the automatic knot tying process and result in unable to successfully separate from the clamping member 34 to perform knot tying at the opening 322.

As a conclusion, the invention relies on the two needle threading arms 50 and the two thread drawing modules 40 to draw the surgical suture 10 reciprocally in the threading module 30 to tie the knot on the surgical suture 10 at the opening 322. It provides features as follows;

1. Automatic knot tying at the surgery suturing location that can be done without extra exercises of the surgeons, hence the doctors can perform with confidence without prolonged exercises to get the skills needed.

2. Aid the doctors to perform suturing of the wounds during surgical operation to alleviate the burden of the doctors.

What is claimed is:

1. A surgery automatic suturing and knot tying apparatus to suture and tie knots on a surgical suture with a needle end and a tail end, comprising:
   a positioning board including a knot tying side and an operation side at two sides and two thread drawing apertures communicating with the knot tying side and the operation side;
   a threading module which is located on the positioning board between the two thread drawing apertures and includes a threading rack located at the knot tying side and a clamping member connected to the threading rack, the threading rack including a bend section, an opening at one end of the bend section remote from the positioning board and a lower threading space inside the bend section to communicate with the opening, the clamping member being located at one end of the bend section abutting the opening, the bend section and the positioning board being interposed by an upper threading space corresponding to the lower threading space;
   two thread drawing modules located on the positioning board corresponding to the two thread drawing apertures and at two sides of a plane formed by the lower threading space, the two thread drawing modules including respectively a lift mechanism running through the thread drawing aperture and a thread drawing member located on the lift mechanism, the thread drawing member being movable reciprocally between the knot tying side and the operation side through the lift mechanism; and
   two needle threading arms located at two sides of the two thread drawing modules remote from the threading rack and at the knot tying side of the positioning board to swivel about the positioning board serving as an axis towards the threading rack; the clamping member clamping the tail end of the surgical suture, the two needle threading arms alternately holding a needle at the needle end to pass through the upper threading space and the lower threading space of the threading module and collaborate with the two thread drawing modules to tie knots on the surgical suture at the opening.

2. The surgery automatic suturing and knot tying apparatus of claim 1, wherein the positioning board further includes a vertical movement unit connected to the threading rack to control the threading rack to move vertically towards the positioning board.

3. The surgery automatic suturing and knot tying apparatus of claim 2, wherein the threading rack includes an upper threading position remote from the positioning board through the vertical movement of the vertical movement unit and a lower threading position abutting the positioning board;
   wherein at the upper threading position the two needle threading arms alternately hold the needle in the upper threading space;
   wherein at the lower threading position the two needle threading arms alternately hold the needle in the lower threading space to wind the surgical suture around the bend section.

4. The surgery automatic suturing and knot tying apparatus of claim 1 further including two vertical operation units connected to the two needle threading arms to control the two needle threading arms to move vertically towards the positioning board and alternately hold the needle in the upper threading space and the lower threading space.

5. The surgery automatic suturing and knot tying apparatus of claim 1, wherein each thread drawing module further includes a swivel member located on the lift mechanism, the thread drawing member being a rod fixedly located on the swivel member and extended in a direction remote from the lift mechanism, the swivel member driving the thread drawing member to swivel in the moving direction of the lift mechanism.

6. The surgery automatic suturing and knot tying apparatus of claim 1, wherein the two thread drawing modules are located at one side of the positioning board abutting the opening, the thread drawing member being a rod extended from the opening towards the bend section.

7. The surgery automatic suturing and knot tying apparatus of claim 1, wherein the bend section is an arched structure to form the opening.

8. The surgery automatic suturing and knot tying apparatus of claim 1, wherein the threading module further includes a rotary unit connected to the threading rack to allow the threading rack to rotate about the rotary unit serving as an axis.

* * * * *